(12) United States Patent
Bilyeu

(10) Patent No.: US 7,951,537 B2
(45) Date of Patent: May 31, 2011

(54) DEVELOPMENT OF LOW ALLERGEN SOYBEAN SEEDS USING MOLECULAR MARKERS FOR THE P34 ALLELE

(75) Inventor: Kristin D. Bilyeu, Columbia, MO (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 171 days.

(21) Appl. No.: 12/322,033

(22) Filed: Jan. 28, 2009

(65) Prior Publication Data

US 2010/0190154 A1    Jul. 29, 2010

(51) Int. Cl.
*C12Q 1/68* (2006.01)
*C12P 19/34* (2006.01)
*C07H 21/02* (2006.01)
(52) U.S. Cl. ............................ 435/6; 435/91.2; 536/23.1
(58) Field of Classification Search ........................ None
See application file for complete search history.

(56) References Cited

U.S. PATENT DOCUMENTS 6,864,362 B2    3/2005    Kinney

OTHER PUBLICATIONS

GenBank Locus AB013289 (Apr. 29, 1998) 'Glycine max gene for Bd 30K, complete cds.' GI:3097320, from www.ncbi.nlm.nih.gov, printed pp. 1-3.*
Joseph, Leina M., et al., Evaluation of Glycine Germplasm for Nulls of the immunodominant Allergent P34/Gly m Bd 30k, Crop Science, pp. 1755-1763, 46, 2006.

* cited by examiner

*Primary Examiner* — Stephen Kapushoc
(74) *Attorney, Agent, or Firm* — John Fado; Randall E. Deck; Lesley Shaw

(57) ABSTRACT

A mutation in the gene encoding the P34 protein in soybean which affects allergenicity is characterized. Soybean homozygous for a mutant allele comprising a four base pair insertion at the start codon of the gene encoding the P34 protein, exhibit significantly reduced P34 protein accumulation. Nucleic acid samples of soybean may be assayed for the presence of this insertion to detect the mutant allele, and soybean containing the allele may be selected for breeding to generate reduced P34 soybean lines. Molecular markers have been developed for detecting the presence or absence of the four base pair insertion.

7 Claims, 3 Drawing Sheets

DEVELOPMENT OF LOW ALLERGEN SOYBEAN SEEDS USING MOLECULAR MARKERS FOR THE P34 ALLELE

BACKGROUND OF THE INVENTION

1. Field of the Invention

The invention is drawn to molecular markers for mutant alleles of soybean associated with the low P34 allergen phenotypes.

2. Description of the Prior Art

Soybean is an important source of vegetable oil and high protein meal that is incorporated into many foods and feeds, and the use of soybean meal by the food industry is increasing. However, anti-nutritional compounds such as phytate, raffinose family oligosaccharides, and allergenic proteins that accumulate during normal soybean seed development limit the extent to which soybean meal can be included in livestock diet formulations. Livestock such as weanling pigs have been shown to have a sensitivity to soybean meal proteins (Li et al. 1991. Interrelationship between hypersensitivity to soybean proteins and growth performance in early-weaned pigs. J. Anim Sci. 69:4062-4069; and Li et al. 1990. Transient hypersensitivity to soybean meal in the early-weaned pig. J. Anim Sci. 68:1790-1799). For humans too, soybean seeds contain multiple proteins that are considered to be allergenic. The United States Food and Drug Administration recently recognized soybean as one of the major food allergens and new food allergen labeling requirements are in effect.

The dominant or major soybean allergen is Gly m Bd 30K, a papain superfamily cysteine protease-type protein which is also known as P34 (Kalinski et al. 1990. Molecular cloning of a protein associated with soybean seed oil bodies that is similar to thiol proteases of the papain family. J. Biol. Chem. 265:13843-13848; and Ogawa et al. 1993. Identification of the soybean allergenic protein, Gly m Bd 30K, with the soybean seed 34-kDa oil-body-associated protein. Biosci Biotechnol Biochem. 57:1030-3). This protein provoked a response in almost two thirds of patients examined in one study (Ogawa et al. 1991. Investigation of the IgE-binding proteins in soybeans by immunoblotting with the sera of the soybean-sensitive patients with a topic dermatitis. J Nutr Sci Vitaminol (Tokyo). 37:555-65). Although P34 is not an abundant seed protein, it is consistently present in nearly all germplasm accessions evaluated (Joseph et al. 2006. Evaluation of Glycine germplasm for nulls of the immunodominant allergen P34/Gly m Bd 30k. Crop Sci 46:1755-1763; Xu et al. 2007. Proteomic analysis of the distribution of the major seed allergens in wild, landrace, ancestral, and modern soybean genotypes. Journal of the Science of Food and Agriculture 87:2511-2518; and Yaklich et al. 1999. analysis of the distribution of the major soybean seed allergens in a core collection of *Glycine max* accessions. Crop Sci 39:1444-1447).

Transgenic suppression was successful in downregulation of P34 accumulation in soybean seeds with no apparent negative consequences to normal seed development and composition (Herman et al. 2003. Genetic modification removes an immunodominant allergen from soybean. Plant Physiol. 132: 36-43). While the P34 protein failed to accumulate in transgenic seeds, there were no collateral alterations in other seed proteins as assessed by 2D gel electrophoresis. Additionally, the protein storage vacuoles (PSVs) in the P34 suppressed seeds were indistinguishable from those in the control seeds despite the fact that the P34 protein has been shown to accumulate in the PSVs (Herman et al., 2003, ibid).

Recently, large scale screening of approximately 16,000 soybean accessions from the USDA germplasm collections identified only two *Glycine max* lines with reduced P34 protein accumulation in seeds (Joseph et al., 2006, ibid, the contents of which are incorporated by reference herein). *Glycine max* low P34 soybean accessions, PI 567476 and PI 603570A, were characterized as having normal accumulation of seed proteins other than P34 (Joseph et al., 2006, ibid). While these two soybean accessions were shown to accumulate greatly reduced levels of the P34 protein in mature seeds, an understanding of the molecular genetic basis for this trait was lacking.

SUMMARY OF THE INVENTION

I have now discovered a mutation in the gene encoding the P34 protein in soybean which affects allergenicity. Specifically, soybeans homozygous for a mutant allele comprising a four base pair insertion at the start codon of the gene encoding the P34 protein thereby generating a direct repeat TATG-TATG sequence that includes (encompasses) the wild-type ATG start codon, exhibit significantly reduced P34 protein accumulation. Nucleic acid samples of soybean may be assayed for the presence of this insertion to detect the mutant allele, and soybean containing the allele may be selected for breeding to generate reduced P34 soybean lines. Molecular markers have been developed for detecting the presence or absence of the four base pair insertion.

In accordance with this discovery, it is an object of this invention to provide a method for identifying soybean germplasm containing a mutant P34 allele associated with reduced accumulation of the P34 allergenic protein.

A further object of this invention is to provide a method for identifying soybean germplasm containing this mutant P34 allele for use in breeding to develop low P34 soybean lines.

Another object of this invention is to provide a method for identifying soybean germplasm containing this mutant P34 allele which comprises a four base pair insertion at the start codon of the gene encoding the P34 protein.

Yet another object of this invention is to characterize the molecular genetic basis for the low P34 levels in soybean accessions PI 567476 and PI 603570A.

Still another object of this invention is to provide molecular markers for detecting the the mutant P34 allele associated with reduced accumulation of the P34 allergenic protein in germplasm.

Other objects and advantages of this invention will become readily apparent from the ensuing description.

Figure 2:
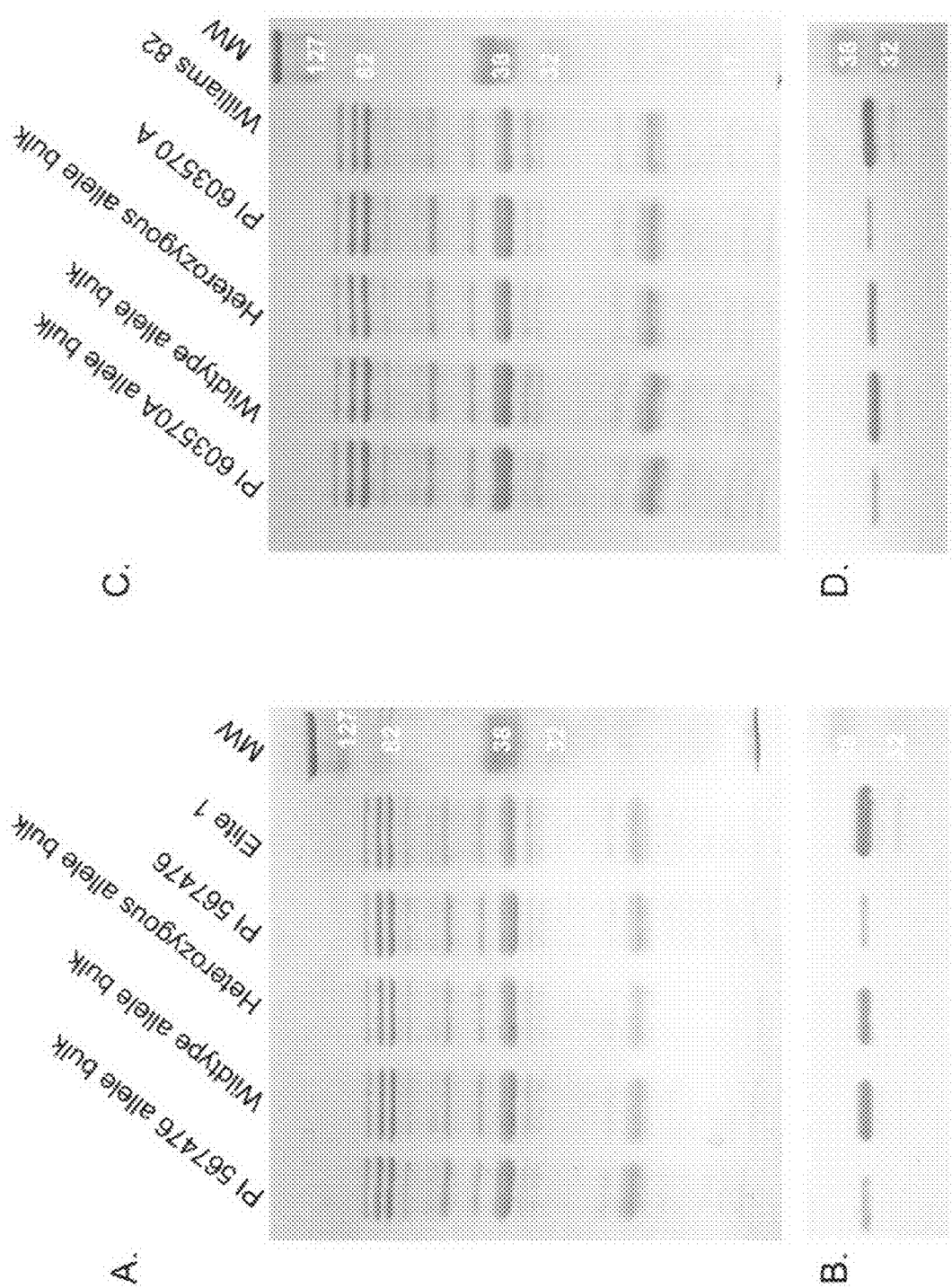

FIG. 2 shows the association of the low P34 phenotype with the PI 567476 and PI 603570A P34 four base pair insertion alleles. (A) Coomassie Blue stained total seed proteins extracted from ground bulk seed samples and separated by SDS-PAGE from population 1 and the parental lines PI 567476 and Elite 1. The allele bulks consisted of mixed ground seed from the indicated genotype class listed and each lane represents the proteins extracted from 50 µg of dried seed corrected for dilution. MW indicates protein molecular weight standards, and the individual proteins are labeled with their apparent molecular mass. (B) Western blot with anti-P34 monoclonal antibodies on duplicate gel, as in panel A. (C) Coomassie Blue stained total seed proteins extracted from ground bulk seed samples and separated by SDS-PAGE from population 2 and the parental line PI 603570A as well as the wild-type P34 cultivar Williams 82. Each lane is labeled similar to those in panel A. (D) Western blot with anti-P34 monoclonal antibodies on duplicate gel, as in panel C.

Figure 3:
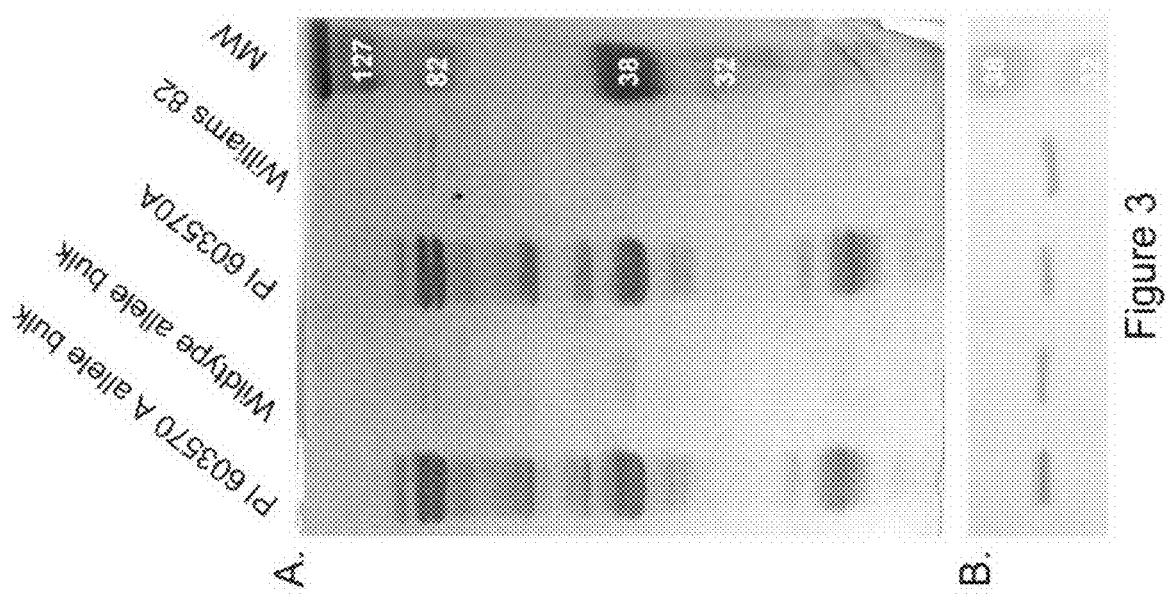

FIG. 3 shows the reduction of P34 protein level in four base pair insertion P34 lines. (A) Coomassie Blue stained total seed proteins extracted from ground bulk seed samples representing 50 µg dry ground seed and separated by SDS-PAGE from the PI 603570A and the mutant P34 allele bulk sample from population 2. The cultivar Williams 82 and the wild-type P34 allele bulk samples were diluted an additional 8-fold (representing 6.25 µg dried seed). The allele bulks consisted of mixed ground seed from the indicated genotype class. MW indicates protein molecular weight standards, and the individual proteins are labeled with their apparent molecular mass. (B) Western blot with anti-P34 monoclonal antibodies on duplicate gel, as in panel A.

DEFINITIONS

Allele: the term coined by Bateson and Saunders (1902) for characters which are alternative to one another in Mendelian inheritance (Gk. Allelon, one another; morphe, form). Now the term allele is used for two or more alternative forms of a gene resulting in different gene products and thus different phenotypes. In a haploid set of chromosomes there is only one allele at its specific locus. Diploid organisms have 2 alleles at a given locus, and if they are homozygous for a defined gene, both alleles are identical. However, if heterozygous for a defined gene they have one normal and one mutant allele. A single allele for each gene locus is inherited separately from each parent (e.g., at a locus for eye color the allele might result in blue or brown eyes). An organism is homozygous for a gene if the alleles are identical, and heterozygous if they are different. (Birgid Schlindwein's Hypermedia Glossary of Genetic Terms).

Amplicon: a term to define the amplification product generated by the polymerase chain reaction. The physical boundaries of an amplicon extend to the base sequence at the 5' ends of each of a pair of primers (short, 18-20 oligonucleotides) in the reaction.

Centimomorgan (cM): a unit to measure the recombination frequency. One centimorgan is equal to a 1% chance that a marker at one genetic locus will be separated from a marker at a second locus due to crossing over in a single generation. In human beings, 1 centimorgan is equivalent, on average, to 1 million base pairs. (Birgid Schlindwein's Hypermedia Glossary of Genetic Terms).

Crossing over: the term coined by Morgan and Cattell (1912) for the occurrence of new combinations of linked characters. With the acceptance of the chromosome theory, the term is applied to the breaking during meiosis of one maternal and one paternal chromosome, the exchange of corresponding sections of DNA, and the rejoining of the chromosomes. This process can result in an exchange of alleles between chromosomes and gives rise to new character combinations. (Birgid Schlindwein's Hypermedia Glossary of Genetic Terms).

DNA or RNA sequence: a linear series of nucleotides connected one to the other by phosphodiester bonds between the 3' and 5' carbons of adjacent pentoses.

Genotype: the term proposed by Johannsen (1909) for the hereditary constitution of an individual, or of particular nuclei within its cells. (Birgid Schlindwein's Hypermedia Glossary of Genetic Terms).

Identity by descent: two alleles at a single locus are identical by descent if there are identical copies of the same allele in some earlier generation, i.e., both are copies that arose by DNA replication from the same ancestral sequence without any intervening mutation. The organism is homozygous for this defined locus.

Identity by type: two alleles at a single locus are identical by type, (i.e. "the same") if they have the same phenotypic effects.

Locus: the position of a gene on a chromosome or other chromosome markers; also, the DNA at that position. The use of the term locus is sometimes restricted to main regions of DNA that are expressed. (Birgid Schlindwein's Hypermedia Glossary of Genetic Terms).

Marker: an identifiable physical location on a chromosome (e.g., restriction enzyme cutting site, gene, minisatellite, microsatellite) whose inheritance can be monitored. Markers can be expressed regions of DNA (genes) or some segment of DNA with no known coding function but whose pattern of inheritance can be determined. (Birgid Schlindwein's Hypermedia Glossary of Genetic Terms).

Nucleic acid: a deoxyribonucleotide or ribonucleotide polymer in either single- or double-stranded form, including known analogs of natural nucleotides unless otherwise indicated.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

Oligonucleotide: a single-stranded nucleic acid ranging in length from 2 to about 500 bases, usually 2-100 bases.

Phenotype: the term coined by Johannsen (1909) for the appearance (Gk. phainein, to appear) of an organism with respect to a particular character or group of characters (physical, biochemical, and physiologic), as a result of the interaction of its genotype and its environment. Often used to define the consequences of a particular mutation. (Birgid Schlindwein's Hypermedia Glossary of Genetic Terms).

Polymorphic marker or site: the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild-type form. Diploid organisms may be homozygous or heterozygous for allelic forms. A diallelic polymorphism has two forms. A triallelic polymorphism has three forms (U.S. Pat. No. 6,368,799).

Probe: a DNA fragment or an oligonucleotide capable of binding to a target nucleic acid of complementary sequence through one or more types of chemical bonds, by hybridization or complementary base pairing, usually through hydrogen bond formation. Oligonucleotides probes are often 10-50 or 15-30 bases long. An oligonucleotide probe may include natural (i.e. A, G, C, or T) or modified bases (7-deazaguanosine, inosine, etc.).

Recombination: the process by which progeny derive a combination of linked genes different from that of either parent. In higher organisms, this can occur by crossing over between their loci during meiosis. Recombination may come about through random orientation of non-homologous chromosome pairs on the meiotic spindles, from crossing-over between homologous chromosomes, from gene conversion, or by other means. (Birgid Schlindwein's Hypermedia Glossary of Genetic Terms).

Single nucleotide polymorphism (SNP): occurrence of a polymorphic site occupied by a single nucleotide, constituting the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site.

Specific hybridization: binding, duplexing, or hybridizing of a molecule only to a particular nucleotide sequence under stringent conditions such that the probe will hybridize to its target subsequence, but not to other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. A perfectly matched probe has a sequence perfectly complementary to a particular target sequence (U.S. Pat. No. 6,368,799).

Transition: the term proposed by Freese (1959) for a mutation caused by the substitution in DNA or RNA of one purine by the other, and similarly with the pyrimidines. (Birgid Schlindwein's Hypermedia Glossary of Genetic Terms).

Transversion: the term proposed by Freese (1959) for a mutation caused by the substitution of a purine for a pyrimidine, and vice versa, in DNA or RNA. (Birgid Schlindwein's Hypermedia Glossary of Genetic Terms).

GENBANK DEPOSIT

The genomic sequence for the P34 allele for soybean cultivar Williams 82 has been deposited in GenBank under accession no. FJ616287 (the contents of which are incorporated by reference herein). The genomic sequence for the P34 allele for low P34 soybean cultivars PI 567476 and PI 603570A (Joseph et al., 2006, ibid) has been deposited in GenBank under accession number FJ616288 (the contents of which are incorporated by reference herein).

DETAILED DESCRIPTION OF THE INVENTION

Figure 1:
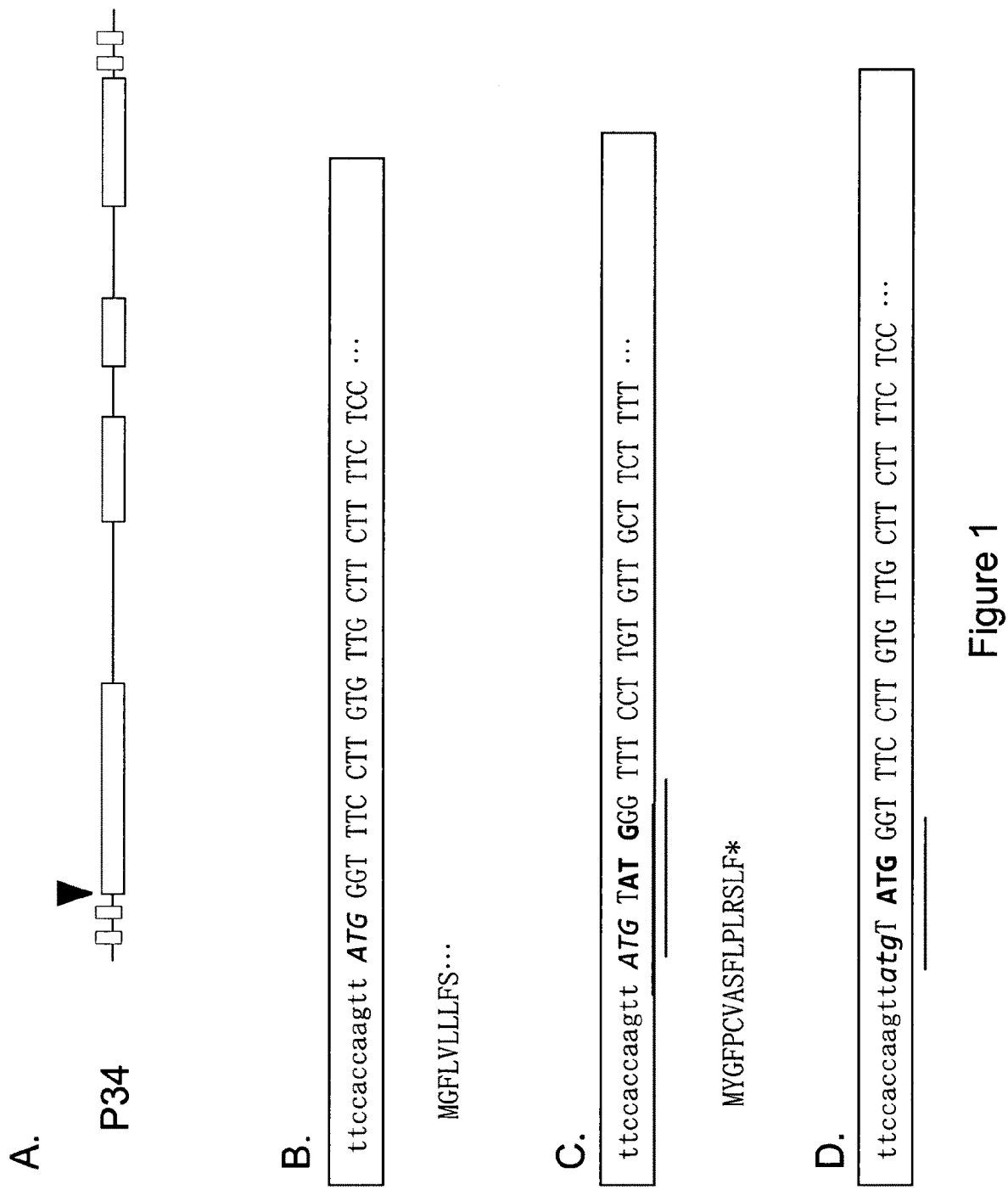
FIG. 1 shows the genomic organization of the P34 gene for Williams 82 and low P34 soybean accessions PI 567476 and PI 603570A. (A) Four exons (open boxes) and three introns (lines separating exons) were assembled from trace archive sequence reads and amplification and sequencing of Williams 82 genomic DNA in the P34 gene region. Short sequences of 5' and 3' untranslated regions were also amplified and sequenced as represented by dashed lines. At the start codon of the P34 allele of the low P34 accessions, a four base pair insertion results in a direct sequence repeat (TATGTATG). The position of the insertion is represented by a solid triangle. (B) Positions 212-253 of the wild-type sequence (SEQ ID NO: 2) of the P34 gene in the start codon region. 5' untranslated nucleotides are in lowercase letters, the start codon ATG is in italics, and the translated nucleotides are in uppercase letters, with each codon separated by a space. Only the first ten codons are represented. Below the nucleotide sequence is a translation of the first ten amino acids of the wild-type P34 protein (SEQ ID NO: 19). (C) Mutant sequence of the P34 allele (SEQ ID NO: 1) at positions 212-253 of the sequence in the start codon region. One possible effect of the P34 four base pair insertion allele (the direct repeat is underlined) is translation initiation at the first ATG (italics) and a frameshift producing a 17 amino acid peptide. The second ATG is listed in bold, and the sequence only represents the first ten codons. The four base pair insertion TATG immediately follows the wild-type ATG start codon. Below the nucleotide sequence is the frameshifted peptide that would result from translation of the mutant P34 allele (SEQ ID NO: 20). (D) Mutant sequence of the P34 allele (SEQ ID NO: 1) at positions 212-257 of the sequence in the start codon region. Another possible effect of the P34 four base pair insertion is a reduction or elimination of translation initiation at the second ATG (bold) due to sequence changes just upstream from the start codon, including an additional ATG (italics). The four base pair insertion ATGT immediately precedes the wild-type ATG start codon.

As noted hereinabove, the genomic sequence for the P34 allele for low P34 soybean cultivars PI 567476 and PI 603570A has been deposited in GenBank under accession number FJ616288 and is presented herein as SEQ ID NO: 1. The genomic sequence for the P34 allele for soybean cultivar Williams 82 (which is the consensus or wild type sequence for the P34 gene) has been deposited in GenBank under accession no. FJ616287, and is presented herein as SEQ ID NO: 2. The typical or consensus wild-type sequence encoding the P34 protein contains an ATG start codon as shown in FIG. 1(B). I have surprisingly discovered that the low P34 cultivars PI 567476 and PI 603570A, which were previously identified by Joseph et al. (2006, ibid), each contain a four base pair insertion at the P34 start codon, which results in a short direct repeat (TATGTATG) that includes the original P34 start codon. This four base pair insertion may be either a TATG inserted immediately after the wild-type ATG start codon (in the 5' to 3' direction of the coding strand as shown in FIG. 1(C)), or an ATGT inserted immediately before the wild-type ATG start codon (in the 5' to 3' direction of the coding strand as shown in FIG. 1(D)). In either event, the last seven bases of the resultant TATGTATG repeat (i.e., ATGTATG) immediately follow the 3' end of the non-translated ttccaccaagtt sequence (SEQ ID NO: 21) of FIG. 1 and SEQ ID NO: 2. No other sequence differences were observed in the P34 genomic DNA region between the two low P34 germplasm cultivars and the genomic sequence of the standard cultivar Williams 82. In addition, when the P34 genomic DNA region from the cultivar Century was sequenced, the results were identical to the Williams 82 sequence and indicated that the original Century P34 cDNA sequence (GenBank accession J05560) may have contained some errors. The P34 allele containing the four base pair insertion also has not been detected from a subset of ancestral soybean lines (Sneller, 1994. Pedigree analysis of elite soybean lines. Crop Science 34:1515-1522) or from any other lines unrelated to the two low allergen accessions mentioned hereinabove.

As described in Example 1, inheritance of the PI 567476 and PI 603570A mutant P34 alleles completely associated with the low P34 seed phenotype in independent segregating populations. When segregating populations were developed from crosses between elite lines containing wild-type levels of the P34 protein and the low P34 lines PI 567476 and PI 603570A, populations which were homozygous for the mutant P34 allele (i.e. SEQ ID NO: 1) produced seeds with the low P34 phenotype, similar to the low P34 phenotype from the PI 567476 and PI 603570A cultivars. In contrast, populations which were either heterozygous or homozygous for the wild-type P34 allele (i.e. SEQ ID NO: 2) exhibited no significant reduction in P34 protein levels in comparison to the wild-type levels. Thus, the detection of soybean homozygous for the mutant allele containing the four base pair insertion at the start codon of the gene encoding the P34 protein is indicative of reduced P34 protein accumulation in the soybean. Accordingly, assays for the detection of this mutant allele may be used to select germplasm for breeding to produce low P34 lines homozygous for the mutant allele.

The invention is drawn to a method for determining alleles of the gene encoding the allergenic P34 protein in soybean, *Glycine max* (L.) Merr. In accordance with this method, a sample of nucleic acid molecules from a soybean is assayed for the presence of the above-described four base pair insertion at the start codon of the gene encoding the P34 protein. As noted hereinabove, this four base pair insertion results in a direct repeat TATGTATG sequence that includes the wild-type or normal ATG start codon.

Mutant alleles associated with the low P34 seed phenotype may be detected by assaying for the presence of the above-mentioned insertion at the start codon of the gene encoding the P34 protein in a sample of nucleic acids from soybean germplasm. Suitable nucleic acids for use in the assay include genomic DNA, cDNA, or RNA, as well as nucleic acids that encompass, or are encompassed by, SEQ ID NO: 1 and SEQ ID NO: 2, or the complement thereof. However, the use of genomic DNA molecules is preferred. Sample materials which may be collected from the soybean for the assay include, but are not limited to, seeds, leaves, cells or other biological samples from the subject.

The presence of the mutant allele can be determined by any of a number of molecular marker assays. These assays may use otherwise known techniques, including direct sequencing of the nucleic acids in the sample, or using probes which overlap the position of the start codon for the gene encoding P34 on those nucleic acids. For example, suitable assays include, but are not limited to, ligase based methods are described by Barany et al. (1997) WO 97/31256 and Chen et al. Genome Res. 1998; 8(5):549-556; mass-spectroscopy-based methods by Monforte (1998) WO 98/12355, Turano et al. (1998) WO 98/14616 and Ross et al. (1997) Anal. Chem. 15:4197-4202; PCR-based methods such as disclosed by Hauser, et al. (1998) Plant J. 16:117-125; exonuclease-based methods by Mundy U.S. Pat. No. 4,656,127; dideoxynucleotide-based methods by Cohen et al. WO 91/02087; Genetic Bit Analysis or GBA by Goelet et al. WO 92/15712; Oligonucleotide Ligation Assays or OLAs by Landegren et al. (1988) Science 241:1077-1080 and Nickerson et al. (1990) Proc. Natl. Acad. Sci. (USA) 87:8923-8927; and primer-guided nucleotide incorporation procedures by Prezant et al. (1992) Hum. Mutat. 1:159-164; Ugozzoli et al. (1992) GATA 9:107-112; Nyreen et al. (1993) Anal. Biochem. 208:171-175, all of which are incorporated herein by reference. Northern Blot analysis is preferred for analysis of RNA samples.

In accordance with a preferred embodiment, the presence of the mutant allele is detected by PCR amplification or melting curve analysis as described in Example 1. It is envisioned that a variety of primers and PCR assays may be suitable for use in the amplification, although preferred primers for use herein are described in Example 1.

The four base pair insertion in the start codon of the gene encoding the P34 protein may be used as a marker for identifying soybean associated with reduced P34 accumulation. In a preferred embodiment, the insertion is used as a marker to select for soybean having the mutant allele associated with reduced P34 accumulation for use in breeding programs to produce progeny which will exhibit significantly reduced accumulation of P34 proteins relative to soybean possessing the wild-type alleles for P34. Soybean germplasm identified as possessing the mutant allele, would be retained for breeding to incorporate the low P34 trait into elite germplasm such as through backcross breeding.

The following example is intended only to further illustrate the invention and is not intended to limit the scope of the invention which is defined by the claims.

EXAMPLE 1

Materials and Methods

DNA Sequencing

Genomic DNA was isolated from leaves of Williams 82, PI 567476, PI 603570A, and Century using the DNeasy Plant Mini Kit (Qiagen, Inc., Valencia, Calif.) and used at 5 to 50 ng per PCR amplification. Primers were designed to amplify P34 products covering the entire genomic sequence [Jp34G1: CCCCTGCTGGATAATGAAAA (SEQ ID NO: 3) and P34R1:AATCCCATGATGCAGGTGGA (SEQ ID NO: 4); p347:AGCAAATCAAAATGGCCAAC (SEQ ID NO: 5) and p348:TGGCTTTGCATCTACCCTCT (SEQ ID NO: 6); 34-5:GCACATGCAATAGCAACAGG (SEQ ID NO: 7) and 34-6:ACGGCTCAAAGAGGAGAGTG (SEQ ID NO: 8); Jp343pr1:GTCTGCTCGCGTTAAAGGTC (SEQ ID NO: 9) and Jp343pr2:TGCTTGCACAATGGAAAGAG (SEQ ID NO: 10); as well as P349:CCCAACCAAAGAGGAATCAG (SEQ ID NO: 11) and P3410:TGAAGCATGCATGT-TGAAGA (SEQ ID NO: 12)]. PCR products were analyzed by gel electrophoresis to ensure specific amplification. PCR products were isolated with the Qiaprep Spin Miniprep kit (Qiagen, Inc.) and sequenced with each of the amplification primers at the University of Missouri DNA Core facility.

Molecular Marker Assays and Genotyping

Molecular marker assays were designed to differentiate between wild-type P34 start codon region alleles and the PI 567476/PI 603570A four base-pair insertion alleles. The P34 GC tail assay (Wang et al., 2005. High-throughput SNP genotyping by single-tube PCR with Tm-shift primers. Biotechniques 39:885-93) utilized three primers: xp34F1:GCTA-CAAGTGAAGTGACCATATC (SEQ ID NO: 13); x341: gcgggcACAAGGAAACCCATAACTTGG (SEQ ID NO: 14); and x342: gcgggcagggcggcACAAGGAAAC-CCATACATAACTTG (SEQ ID NO: 15). Reactions were carried out in 15 µl; each primer was at 0.375 µM final concentration in reactions containing template, buffer (40 mM Tricine-KOH (pH 8.0), 16 mM KCl, 3.5 mM $MgCl_2$, 3.75 µg $ml^{-1}$ BSA, 200 µM dNTPs), 5% DMSO, 0.25×SYBR Green I, and 0.2×Titanium Taq polymerase (BD Biosciences, Palo Alto, Calif.). PCR parameters on a DNA Engine Opticon 2 (MJ Research/Bio-Rad, Hercules, Calif.) for the P34 GC Tail assay were as follows: 95° C. for 5 minutes followed by 35 cycles of 95° C. for 20 seconds, 64° C. for 20 seconds, 72° C. for 20 seconds, and then a melting curve from 72° C. to 85° C. The fluorescence was read after each cycle and every 0.2°

C. with a one second hold during the melt with excitation at 470-505 nm and detection at 523-543 nm. Each genotype produced a product with a characteristic melting profile, as measured by Tm of the negative first derivative of the disappearance of fluorescent signal. Homozygous wild-type P34 samples produced a peak at 75° C., homozygous mutant P34 alleles produced a peak at 77° C., and heterozygous P34 alleles produced a peak at 77° C. with a shoulder at 75° C.

The P34 size assay relied on detecting the four base-pair difference in PCR product sizes for wild-type and mutant P34 alleles. The assay utilized two primers: P34f:CTCACTAAT-CACTATATATACGACATGC (SEQ ID NO: 16), which was 6-FAM (fluorescein)-labeled on the 5' end; and P34r:ATG-GAACGATGAGTTGATATGC (SEQ ID NO: 17). Amplification conditions were 95° C. for 5 minutes followed by 35 cycles of 95° C. for 20 seconds, 60° C. for 20 seconds, 72° C. for 20 seconds. PCR was performed as above except in reaction mix without SYBR green I dye, and in 10 μl reactions with 0.5 μM each primer. PCR products were diluted 1:50 in water; 1.5 μl of diluted products were sized on an ABI 3730 DNA analyzer at the University of Missouri DNA Core facility. Wild-type P34 products were 157 bp, mutant products were 161 bp, and heterozygous samples contained both products.

The P34 SimpleProbe assay was based on the disassociation kinetics of an oligonucleotide SimpleProbe (Roche Applied Sciences, Indianapolis, Ind.) corresponding to the mutant P34 sequence encompassing the four base pair insertion (Fluorescein-SPC-CACCAAGTTatgtATGGGTTTC-CTTGTGTT-phosphate)(SEQ ID NO: 18). The assay utilized the same amplification conditions, the general reaction mixture without SYBR green I dye, and the same primers used in the P34 size assay, except P34f was not 6-FAM-labeled. Amplification reactions (20 μl) consisted of an asymmetric mixture of the amplification primers: 0.2 μM P34f and 0.5 μM P34r. The P34 SimpleProbe was included at 0.2 μM. The disassociation kinetics of the SimpleProbe were assessed following the PCR with the inclusion of a melting curve. For the LightCycler 480 Real-Time PCR System (Roche Applied Sciences), wild-type samples produced a peak at 59° C., mutant samples produced a peak at 66° C., and heterozygous samples produced both peaks. For the DNA Engine Opticon 2 (Bio-Rad), wild-type samples produced a broad peak at 58° C., mutant samples produced a peak at 65° C., and heterozygous samples contained both peaks.

Plant Materials/Population Development

Two segregating populations were developed from crosses between conventional, P34—containing soybean germplasm and the low P34 soybean accessions described previously (Joseph et al., 2006, ibid): Population 1 (Elite 1×PI 567476) and population 2 (Elite 2×PI 603570A). $F_2$ plants were grown at the Bradford Research and Extension Center located near Columbia, Mo. in 2007. Parental lines were grown at the same time and location with exception of Elite 2, for which Williams 82 was substituted as a wild-type P34 line. Fifty $F_2$ plants were chosen at random from population 1 and 100 plants from population 2; each plant was tagged, and a single leaflet was harvested from each plant and prepared as an FTA card press (Whatman, Clifton, N.J.). For population 1 lines that produced seed, 8 lines were genotyped homozygous wild-type, 9 were homozygous mutant, and 24 were heterozygous. For population 2 lines that produced seed, 24 were genotyped homozygous wild-type, 16 were homozygous mutant, and 49 were heterozygous. When plants reached maturity, approximately 20 $F_{2:3}$ seeds were harvested from each tagged plant in the two populations.

$F_3$ Seed Genotype and Phenotype Experiment

One $F_2$ plant from population 1 that was heterozygous for the mutant P34 allele was threshed at maturity and forty. individual $F_{2:3}$ seeds were chipped with a scalpel to provide proteins for Western analysis while allowing the remainder of the seed to be germinated and provide leaf tissue for genotyping.

For protein extraction, each approximately 10 mg seed chip in a 1.5-ml tube was combined with 250 μl 1×SDS sample buffer (80 mM Tris-Cl, pH 6.8, 2% SDS, 10% glycerol, 0.7 M 2-mercaptoethanol, and 0.02 g $L^{-1}$ bromophenol blue), and the samples were incubated for 30 minutes at room temperature. Plastic pestles were used to carefully macerate seed chips in sample buffer in the tubes. Samples were incubated at 90° C. for ten minutes prior to centrifugation for 5 minutes at 16,000×g. Samples were diluted 100-fold by transfer of 5 μl of supernatant to 495 μl 1×SDS sample buffer in a fresh tube. Diluted samples were stored at −20° C. Prior to loading 5 μl of each sample on a 12.5% acrylamide SDS PAGE gel (Bio-Rad Protean system, Hercules, Calif.), samples were heated to 90° C. for five minutes and briefly centrifuged. Kaleidoscope Prestained Standards (Bio-Rad) were overlaid in one well per gel. Separated proteins were transferred from the gel to an ImmobilonP transfer membrane (Millipore, Billerica, Mass.) according to the manufacturer's instructions. Westerns utilizing monoclonal anti-P34 antibodies were performed essentially as described for 'Immunoblotting for P34' (Joseph et al., 2006, ibid), except the primary antibodies were diluted 1:2500. After the processed membranes dried, the forty samples on four membranes were subjected to blinded scoring for either high or low intensity P34 bands by three individuals. There was consensus scoring with one exception. That sample was subjected to an independent Western analysis, and was confirmed to be a high intensity P34 sample.

Seed portions containing the embryo were germinated in germination packets (CYG, Mega International, St. Paul, Minn.). Approximately eight to twelve days after imbibition, one unifoliate leaf from each seedling was pressed onto an FTA card (Whatman, Clifton, N.J.). Templates for all genotype PCRs consisted of 1.2 mm washed FTA card punches prepared according to the manufacturer's instructions. Genotypes were obtained using the GC tail assay.

Genotype Bulk Experiment

Population 1 and Population 2 $F_2$ lines were assigned a P34 genotype using the P34 GC tail assay. For each population, three $F_{2:3}$ seeds from each line were combined within each genotype class to create a bulk seed sample representing homozygous mutant, homozygous wild-type and heterozygous P34 genotype classes. Seeds from each genotype class were ground together in a small grinder (SmartGrind, Black & Decker Corp., Towson, Md.). In a 1.5 ml tube, 25 mg of each seed sample was combined with 250 μl of 1×SDS sample buffer, vortexed thoroughly, and heated in a boiling water bath for 5 minutes prior to centrifugation for 5 minutes at 16,000×g. The supernatants were subsequently diluted 25-fold in 1×SDS sample buffer. Diluted samples were stored at −20° C. Prior to loading 5 μl of each sample on each of two 12.5% acrylamide SDS PAGE gels, samples were heated to 90° C. for five minutes and briefly centrifuged. Kaleidoscope Prestained Standards (Bio-Rad) were used in one well per gel. After protein separation, one gel was processed for Western analysis with the P34 antibodies as described above. The duplicate gel was stained with Coomassie Blue R-250 to visualize protein bands.

Results

Identification and characterization of P34 gene sequences from soybean cultivars 'Williams 82' and 'Century', and low P34 allergen germplasm accessions PI 567476 and PI 603570A The Century P34 cDNA sequence (Genbank accession J05560; Kalinski et al., 1990, ibid; the contents of each of which are incorporated by reference herein) was initially used in blast searches of the soybean draft genome sequence trace archives in Genbank to identify the soybean genomic DNA region containing the P34 gene. Individual overlapping sequence traces were used to assemble the consensus P34 gene region from Williams 82. The Williams 82 P34 gene consisted of four exons separated by three introns and encompassed 1806 base pairs from start to stop codons (FIG. 1). The Williams 82 P34 genomic region was identical to a genomic DNA sequence annotated without a cultivar description as 'Glycine max gene for Bd 30K' from GenBank accession AB013289. The Century P34 cDNA sequence deposited as GenBank accession J05560 had several polymorphisms when compared to the exons from the assembled Williams 82 P34 genomic DNA region.

In addition to what appeared to be the authentic P34 gene, two P34 pseudogenes were identified from manual assembly of the soybean trace archive sequences; one P34 pseudogene matched a DNA sequence annotated as 'Glycine max pseudogene for Bd 30K' from GenBank accession AB013290. Although the DNA sequence identity between the P34 sequences was above 90%, this P34 pseudogene contained an inframe stop codon after the first 59 amino acids. Manual analysis of the soybean trace archive sequences and subsequent analysis of the 7× assembly of the soybean genome sequence revealed an additional P34 pseudogene located approximately 10 kilobases away from the authentic P34 gene. This pseudogene contained a stop codon following the first 142 amino acids. The authentic P34 gene (Glycine max 1.01 assembly: Glyma08g12270.1) and one of the pseudogenes (Glyma08g12280.1) were found to reside between microsatellite markers Sat_157 and Sat_212, which corresponded to linkage group A2 (chromosome 08) near the I locus. The pseudogene identical to GenBank accession AB013290 (Glyma05g29104.1) appeared to reside on linkage group A1 (chromosome 05). There was no evidence in the EST collection for expression of either P34 pseudogenes.

Using the Williams 82 P34 genomic sequence, PCR primers were designed to amplify the P34 gene region in overlapping segments from genomic DNA. PCR products corresponding to the P34 region from 267 base pairs upstream from the start codon to 256 base pairs beyond the stop codon were amplified and sequenced from Williams 82, Century, PI 567476 and PI 603570A genomic DNA. Williams 82 and Century P34 sequences were identical to the sequence predicted from trace archives. Alleles for the PI 567476 and PI 603570A P34 gene contained an identical four base pair insertion at the start codon (FIG. 1). The insertion resulted in a short direct repeat (TATGTATG) that included the original P34 start codon. Genomic sequences for the P34 alleles were deposited in GenBank under accession no. FJ616287 for Williams 82 and FJ616288 for PI 567476 and PI 603570A. No other sequence variations were identified among lines in the P34 gene region.

Without wishing to be bound by theory, the four base pair insertion present in the P34 alleles of PI 567476 and PI 603570A could result in several possible outcomes: translation initiation from the first ATG codon and a frameshift that would produce a small 17 amino acid peptide, disruption of the translation initiation site due to the change in sequence and the presence of two start codons resulting in no or reduced translation; or unaltered translation of the P34 gene (FIG. 1). Thus, the PI 567476 and PI 603570A P34 alleles can be considered mutant alleles when compared to the wild-type P34 gene allele present in Williams 82.

Development of Molecular Marker Assays for PI 567476 and PI 603570A P34 Alleles

Sequence information for two P34 pseudogenes, the authentic P34 gene, and the PI 567476 and PI 603570A alleles of the P34 gene were used to design several different molecular marker assays for analysis of the P34 genotype. One assay (P34 GC tail assay) was based on allele-specific PCR amplification in the presence of the dye Sybr Green I of the wild-type or mutant alleles of P34; discrimination of PCR products was accomplished by generation of characteristic melting profiles for the PCR products resulting from inclusion of GC tails in the allele-specific PCR primers (Chappell and Bilyeu. 2007. The Low Linolenic Acid Soybean Line PI 361088B Contains a Novel GmFAD3A Mutation. Crop Sci 47:1705-1710; and Wang et al., 2005, ibid; the contents of each of which are incorporated by reference herein). This assay reliably distinguished plants containing mutant P34 alleles from those that were homozygous for the wild-type P34 alleles and those that were heterozygous for the P34 alleles, although results were best with highly purified DNA templates.

A second molecular marker assay was developed that took advantage of the insertion of four base pairs in the P34 gene in the mutant allele (P34 size assay). PCR primers were designed to specifically amplify the region surrounding the P34 start codon. One primer was fluorescently labeled and the PCR amplification products were diluted and subjected to fragment analysis to determine the exact size of PCR products, which differed by four base pairs depending on the P34 alleles that were present. This assay was robust from different types of DNA templates but required post-PCR processing.

The third molecular marker assay was based on melting curve analysis of a Roche SimpleProbe designed to the mutant P34 allele (SimpleProbe assay). The region surrounding the four base pair insertion was amplified asymmetrically in the presence of the P34-SimpleProbe, and following amplification, the products were subjected to a melting curve analysis. Each genotype class produced a characteristic melting curve profile that was distinguishable on the Roche 480 LightCycler and a standard real-time PCR instrument (Bio-Rad Opticon 2).

The P34 GC tail assay was used to investigate the occurrence of the mutant P34 allele in a subset of the soybean lines that were major contributors to the North American elite soybean germplasm pool (Gizlice et al. 1994. Genetic base for north American public soybean cultivars released between 1947 and 1988. Crop Science 34:1143-1151; and Sneller, 1994, ibid). None of the seventeen "ancestral" soybean lines contained the PI 567476/PI 603570A mutant P34 allele.

Association Analysis of $F_3$ Genotypes and $F_3$ Seed Phenotypes in a Population Segregating for the Low Allergen Trait The mutant allele of the P34 gene in the two identified low P34 lines became the primary candidate for the molecular genetic basis of the low P34 phenotype. To associate the P34 genotype with the P34 protein phenotype, segregating populations were developed from crosses between elite lines containing wild-type levels of the P34 protein and the low P34 lines PI 567476 and PI 603570A. For population 1 (Elite 1×PI 567476) an $F_2$ plant was identified by genotype that was heterozygous for the P34 allele. The $F_{2:3}$ seeds from this heterozygous plant were harvested at maturity. From a subset of seeds, a small portion of each seed was removed with a scalpel (chipped) to provide proteins for Western analysis of the P34 protein; the remainder of each seed was germinated and genotyped with the P34 GC tail assay for either the wild-type, four base pair-insertion P34 allele, or both. For the 40 samples analyzed, the ratio of homozygous wild-type: heterozygous:homozygous mutant P34 genotypes was 7:23: 10.

Phenotypes were determined using P34 monoclonal antibodies and Western blotting of SDS-PAGE-separated total extracted seed chip proteins. Developed Western blots were subjected to blinded scoring for either high or low intensity P34 cross-reacting protein bands. All lines scored to contain low P34 protein were homozygous for the mutant P34 allele genotype. Lines which scored high P34 protein contained either the wild-type or heterozygous P34 genotype.

Association Analysis of Genotype Bulks

Because of variable protein extraction efficiency, seed chips were not the optimum tissue to determine the phenotype for the P34 trait. Therefore, for population 1 and a second population (Elite 2×PI 603570A, population 2), we genotyped $F_2$ plants and harvested their $F_{2:3}$ seeds for phenotypic analysis. Lines were categorized based on their $F_2$ P34 genotype class (homozygous mutant, homozygous wild-type, or heterozygous). Within each of the three genotype classes, three seeds representing each line were combined to make bulks. Proteins were extracted from ground seed samples from each of the classes and analyzed by Western blotting for the P34 protein. The parental lines were included in the Westerns for comparisons. Parental line Elite 2 was not available, so Williams 82 was used as a substitute for the wild-type parent for population 2. In both populations, the results demonstrated that lines which were homozygous for the mutant P34 alleles produced seeds with the low P34 phenotype, similar to their low P34 parent (FIG. 3). Observed differences in P34 protein accumulation between lines that were heterozygous and homozygous for the P34 wild-type allele were not explored further.

Evaluation of Reduction in Seed P34 Protein Levels

Enough seed protein extract was routinely utilized in these experiments to easily detect the P34 protein band in the mutant parental line samples, although at an obviously less intense level than in wild-type samples. When the difference in P34 levels in Westerns after dilution of the wild-type protein samples was evaluated, the P34 band intensities detected from protein extracts of ground whole seed samples were similar when the parental wild-type protein sample was diluted 8-fold compared to the low P34 parent PI 603570A. Apparent differences between the segregating mutant bulk sample and the segregating wild-type samples were also approximately 8-fold when evaluated with dilutions of the wild-type protein sample. Similar differences were observed for the PI 567476 samples compared to wild-type.

Discussion

Results presented here demonstrated the low P34 accessions PI 567476 and PI 603570A each contain an identical four base pair insertion at the P34 start codon. No other sequence differences were observed in the P34 genomic DNA region between the two low P34 germplasm accessions and the genomic sequence of the standard cultivar Williams 82. In addition, when the P34 genomic DNA region from the cultivar Century was sequenced, the results were identical to the Williams 82 sequence and indicated that the original Century P34 cDNA sequence (GenBank accession J05560) may have contained some errors. When the P34 cDNA was amplified and sequenced from the two low P34 germplasm accessions (Joseph et al., 2006, ibid), the forward amplification primer initiated two bases upstream of the original start codon, and thus the resulting product would not have included the four base pair insertion. The P34 allele containing the four base pair insertion has not been detected from a subset of ancestral soybean lines (Sneller, 1994, ibid) or from any other lines unrelated to the two low allergen accessions.

Lack of any reduction in P34 mRNA levels for the two mutant lines (Joseph et al., 2006, ibid) would be consistent with a model in which the P34 protein is mistranslated due to a frameshift, or in which translation initiation is reduced due to alteration of sequence at the start codon. Although two P34 pseudogenes were identified, neither one appeared capable of encoding a full length protein that could account for the P34 band that appeared in Westerns. Indeed, in these experiments, there was an approximately 8-fold reduction in P34 protein accumulation analyzed by Westerns for the two germplasm accessions compared to standard cultivars.

The PI 567476 and PI 603570A P34 alleles were completely associated with the low P34 seed phenotype in independent segregating populations. Molecular marker assays were developed that detected the P34 genotype based on the presence or absence of the four base pair insertion at the start codon. Molecular marker assays were capable of distinguishing homozygous mutant, wild-type, and heterozygous plants. Although the heterozygous seeds seemed to produce an intermediate P34 phenotype, the technical aspects of accurately phenotyping individual heterozygous seeds would be very challenging. Use of the P34 molecular markers for direct selection of the mutant P34 allele would allow the most rapid incorporation of the low P34 trait into elite germplasm through the use of backcross breeding.

It is understood that the foregoing detailed description is given merely by way of illustration and that modifications and variations may be made therein without departing from the spirit and scope of the invention.

I claim:

1. A method for detecting an allele of the gene encoding the P34 protein in a sample from a *Glycine max* (L.) Merr. soybean, said method comprising:
   detecting in a sample of nucleic acid molecules from a *Glycine max* (L.) Merr. soybean, the presence of the direct repeat sequence TATGTATG in the P34 gene at the positions corresponding to positions 223-230 of SEQ ID NO: 1.

2. The method of claim 1 wherein said nucleic acid molecules are selected from the group consisting of genomic DNA, cDNA, and RNA.

3. The method of claim 2 wherein said nucleic acid molecules comprise genomic DNA molecules.

4. The method of claim 1 wherein said nucleic acid molecules comprise a DNA molecule that encompasses, or is encompassed by, the soybean P34 sequence of SEQ ID NO: 1 or SEQ ID NO: 2, or a complement thereof.

5. A method for identifying an allele of a gene encoding the P34 protein in *Glycine max* (L.) Merr. soybean, wherein said allele is indicative of decreased P34 protein accumulation, said method comprising:
   a) obtaining a nucleic acid sample from a *Glycine max* (L.) Merr. soybean; and
   b) detecting in said sample, the presence of the direct repeat sequence TATGTATG in the P34 gene at the positions corresponding to positions 223-230 of SEQ ID NO: 1.

6. The method of claim 5 further comprising selecting those soybean for breeding which comprise said direct repeat sequence.

7. The method of claim 5 wherein said nucleic acid sample is selected from the group consisting of genomic DNA, cDNA, and RNA.

* * * * *

SEQUENCE LISTING

<160> NUMBER OF SEQ ID NOS: 21

<210> SEQ ID NO 1
<211> LENGTH: 2276
<212> TYPE: DNA
<213> ORGANISM: Glycine max

<400> SEQUENCE: 1
tctagtttaa taataaaaaa gttggcaaac tgtcattccc tgttggtttt taagccaaat      60
cacaattcaa ttacgtatca gaaattaatt taaaccaaat atatagctac gagggaactt     120

```
cttcagtcat tactagctag ctcactaatc actatatata cgacatgcta caagtgaagt    180
gaccatatct taatttcaaa tcataaaatt cttccaccaa gttatgtatg ggtttccttg    240
tgttgcttct tttctccctc ttaggtctct cttctagttc cagcatatca actcatcgtt    300
ccatattgga ccttgaccta accaagttta ccacacagaa acaggtgtct tcactgttcc    360
aactatggaa gagtgagcat ggacgtgtct accataacca cgaagaagag gcaaagagac    420
ttgagatttt caagaataac ttgaactata tcagggacta gaatgcaaac agaaaatcac    480
cccattctca tcgtttagga ttgaacaagt ttgctgacat cactcctcaa gagttcagca    540
aaaagtactt gcaagctccc aaggatgtgt cgcagcaaat caaaatggcc aacaagaaaa    600
tgaagaagga acaatattct tgtgaccatc cacctgcatc atgggattgg aggaaaaaag    660
gtgtcatcac ccaagtaaag taccaagggg gctgtggtat gtgaaaccat taattgtttt    720
tactacgtaa ttaccactcc ttctatctta aaataaacag ttgtcttaaa ttgttttata    780
taaattaaaa ataaaataaa ataaaataat atttttacca aactaacctt attagtgaaa    840
gagattacca ttaatactag atttaaaaac taaaaatata tttattagag ttattggtga    900
aaaaaataat taattttacg ttgaaaagtt aaatgtgata tttattttgc tacaattttt    960
tttagtgtga cacttatttt ggaatgggaa ataattatt aacactaact tttttctttt    1020
gtcttgtggt atgtgaaatc attttgatat ataggaagcg gttgggcgtt ttctgccacg    1080
ggagccatag aagcagcaca tgcaatagca acaggagacc ttgttagcct ttctgaacaa    1140
gaactcgtag actgtgtgga agaaagcgaa ggttgttaca atggatggca ctatcaatcg    1200
ttcgaatggg ttttagaaca tggtgggatt gccactgatg atgattatcc ttacagagct    1260
aaagagggta gatgcaaagc caataaggtc tgtgaatata taactgaata atatgcatgc    1320
atgcgattcc ttttaattaa tttaaccctt catctctttg tttaattttg tgcaactttt    1380
tttttttttt ctgggagtag atacaagaca aggttacaat tgacggatat gaaactctaa    1440
taatgtcaga tgagagtaca gaatcagaga cagagcaagc gttcttaagc gccatccttg    1500
agcaaccaat tagtgtctcc attgatgcaa aagattttca tttatacacc ggggtaaagt    1560
aatatcttac tatttgggaa ttattattat tattattata ctatttttt atcggtcaat    1620 tttggtggga aaagattcga aatcatgatt tctttctttt tcggatcatc aaattaacct    1680
catcaattca ttattactgt acagtatact ctatagtatt attgttattg ttgttaattc    1740
attaattaat ttgtgcaggg aatttatgat ggagaaaact gtacaagtcc gtatgggatt    1800
aatcactttg ttttacttgt gggttatggt tcagcggatg gtgtagatta ctggatagcg    1860
aaaaattcat ggggagaaga ttggggagaa gatggttaca tttggatcca agaaacacg    1920 ggtaatttat taggagtgtg tgggatgaat tatttcgctt catacccaac caagaggaa    1980 tcagaaacac tggtgtctgc tcgcgttaaa ggtcatcgaa gagttgatca ctctcctctt    2040
tgagccgtaa aggttcaata caacgagtgc ttgttttctt agggacaagc attgtactta    2100
tgtatgattc tgtgtaacca tgagtcttcc acgttgtact aatgtgaagg gcaaaaataa    2160
aacacagaac aagttcgttt ttctcaaata atgtgaaggt agaaaatgga accatgcctc    2220
ctctcttgca tgtgatttaa aatattagca gatggttttt tctttgcttc atgcct        2276
```

<210> SEQ ID NO 2
<211> LENGTH: 2272
<212> TYPE: DNA
<213> ORGANISM: Glycine max

<400> SEQUENCE: 2

```
tctagtttaa taataaaaaa gttggcaaac tgtcattccc tgttggtttt taagccaaat    60
cacaattcaa ttacgtatca gaaattaatt taaaccaaat atatagctac gagggaactt   120
cttcagtcat tactagctag ctcactaatc actatatata cgacatgcta caagtgaagt   180
gaccatatct taatttcaaa tcataaaatt cttccaccaa gttatgggtt tccttgtgtt   240
gcttcttttc tccctcttag gtctctcttc tagttccagc atatcaactc atcgttccat   300
attggacctt gacctaacca agtttaccac acagaaacag gtgtcttcac tgttccaact   360
atggaagagt gagcatggac gtgtctacca taaccacgaa gaagaggcaa agagacttga   420
gattttcaag aataacttga actatatcag ggacatgaat gcaaacagaa aatcacccca   480
ttctcatcgt ttaggattga acaagtttgc tgacatcact cctcaagagt tcagcaaaaa   540
gtacttgcaa gctcccaagg atgtgtcgca gcaaatcaaa atggccaaca agaaaatgaa   600
gaaggaacaa tattcttgtg accatccacc tgcatcatgg gattggagga aaaaaggtgt   660
catcacccaa gtaaagtacc aaggggggctg tggtatgtga aaccattaat tgtttttact   720
acgtaattac cactccttct atcttaaaat aaacagttgt cttaaattgt tttatataaa   780
ttaaaaataa aataaaataa aataatattt ttaccaaact aaccttatta gtgaaagaga   840
ttaccattaa tactagattt aaaaactaaa aatatattta ttagagttat tggtgaaaaa   900
aataattaat tttacgttga aaagttaaat gtgatattta ttttgctaca attttttta    960 gtgtgacact tattttggaa tgggaaaata attattaaca ctaactttttt ttctttgtct  1020 tgtggtatgt gaaatcattt tgatatatag gaagcggttg ggcgttttct gccacgggag  1080
ccatagaagc agcacatgca atagcaacag gagaccttgt tagcctttct gaacaagaac  1140
tcgtagactg tgtggaagaa agcgaaggtt gttacaatgg atggcactat caatcgttcg  1200
aatgggtttt agaacatggt gggattgcca ctgatgatga ttatccttac agagctaaag  1260
agggtagatg caaagccaat aaggtctgtg aatatataac tgaataatat gcatgcatgc  1320
gattcctttt aattaattta acccttcatc tctttgttta attttgtgca acttttttt    1380 ttttttctgg gagtagatac aagacaaggt tacaattgac ggatatgaaa ctctaataat  1440
gtcagatgag agtacagaat cagagacaga gcaagcgttc ttaagcgcca tccttgagca  1500
accaattagt gtctccattg atgcaaaaga ttttcatttta tacaccgggg taaagtaata  1560
tcttactatt tgggaattat tattattatt attatactat ttttttatcg gtcaattttg  1620
gtgggaaaag attcgaaatc atgatttctt tcttttttcgg atcatcaaat taacctcatc  1680
aattcattat tactgtacag tatactctat agtattattg ttattgttgt taattcatta  1740
attaatttgt gcagggaatt tatgatggag aaaactgtac aagtccgtat gggattaatc  1800
actttgtttt acttgtgggt tatggttcag cggatggtgt agattactgg atagcgaaaa  1860
attcatgggg agaagattgg ggagaagatg gttacatttg gatccaaaga aacacgggta  1920
atttattagg agtgtgtggg atgaattatt tcgcttcata cccaaccaaa gaggaatcag  1980
aaacactggt gtctgctcgc gttaaaggtc atcgaagagt tgatcactct cctctttgag  2040
ccgtaaaggt tcaatacaac gagtgcttgt tttcttaggg acaagcattg tacttatgta  2100
tgattctgtg taaccatgag tcttccacgt tgtactaatg tgaagggcaa aaataaaaca  2160
cagaacaagt tcgttttttct caaataatgt gaaggtagaa aatggaacca tgcctcctct  2220
cttgcatgtg atttaaaata ttagcagatg gttttttctt tgcttcatgc ct          2272

<210> SEQ ID NO 3
<211> LENGTH: 20
<212> TYPE: DNA
```

<213> ORGANISM: Glycine max

<400> SEQUENCE: 3
cccctgctgg ataatgaaaa				20

<210> SEQ ID NO 4
<211> LENGTH: 20
<212> TYPE: DNA
<213> ORGANISM: Glycine max

<400> SEQUENCE: 4
aatcccatga tgcaggtgga				20

<210> SEQ ID NO 5
<211> LENGTH: 20
<212> TYPE: DNA
<213> ORGANISM: Glycine max

<400> SEQUENCE: 5
agcaaatcaa aatggccaac				20

<210> SEQ ID NO 6
<211> LENGTH: 20
<212> TYPE: DNA
<213> ORGANISM: Glycine max

<400> SEQUENCE: 6
tggctttgca tctaccctct				20

<210> SEQ ID NO 7
<211> LENGTH: 20
<212> TYPE: DNA
<213> ORGANISM: Glycine max

<400> SEQUENCE: 7
gcacatgcaa tagcaacagg				20

<210> SEQ ID NO 8
<211> LENGTH: 20
<212> TYPE: DNA
<213> ORGANISM: Glycine max

<400> SEQUENCE: 8
acggctcaaa gaggagagtg				20

<210> SEQ ID NO 9
<211> LENGTH: 20
<212> TYPE: DNA
<213> ORGANISM: Glycine max

<400> SEQUENCE: 9
gtctgctcgc gttaaaggtc				20

<210> SEQ ID NO 10
<211> LENGTH: 20
<212> TYPE: DNA
<213> ORGANISM: Glycine max

<400> SEQUENCE: 10
tgcttgcaca atggaaagag				20

<210> SEQ ID NO 11
<211> LENGTH: 20
<212> TYPE: DNA

```
<213> ORGANISM: Glycine max

<400> SEQUENCE: 11
cccaaccaaa gaggaatcag                                              20

<210> SEQ ID NO 12
<211> LENGTH: 20
<212> TYPE: DNA
<213> ORGANISM: Glycine max

<400> SEQUENCE: 12
tgaagcatgc atgttgaaga                                              20

<210> SEQ ID NO 13
<211> LENGTH: 23
<212> TYPE: DNA
<213> ORGANISM: Glycine max

<400> SEQUENCE: 13
gctacaagtg aagtgaccat atc                                          23

<210> SEQ ID NO 14
<211> LENGTH: 27
<212> TYPE: DNA
<213> ORGANISM: Glycine max

<400> SEQUENCE: 14
gcgggcacaa ggaaacccat aacttgg                                      27

<210> SEQ ID NO 15
<211> LENGTH: 38
<212> TYPE: DNA
<213> ORGANISM: Glycine max

<400> SEQUENCE: 15
gcgggcaggg cggcacaagg aaacccatac ataacttg                          38

<210> SEQ ID NO 16
<211> LENGTH: 28
<212> TYPE: DNA
<213> ORGANISM: Glycine max

<400> SEQUENCE: 16
ctcactaatc actatatata cgacatgc                                     28

<210> SEQ ID NO 17
<211> LENGTH: 22
<212> TYPE: DNA
<213> ORGANISM: Glycine max

<400> SEQUENCE: 17
atggaacgat gagttgatat gc                                           22

<210> SEQ ID NO 18
<211> LENGTH: 30
<212> TYPE: DNA
<213> ORGANISM: Glycine max

<400> SEQUENCE: 18
caccaagtta tgtatgggtt tccttgtgtt                                   30

<210> SEQ ID NO 19
<211> LENGTH: 10
<212> TYPE: PRT
```

```
<213> ORGANISM: Glycine max

<400> SEQUENCE: 19

Met Gly Phe Leu Val Leu Leu Leu Phe Ser
1               5                   10

<210> SEQ ID NO 20
<211> LENGTH: 17
<212> TYPE: PRT
<213> ORGANISM: Glycine max

<400> SEQUENCE: 20

Met Tyr Gly Phe Pro Cys Val Ala Ser Phe Leu Pro Leu Arg Ser Leu
1               5                   10                  15

Phe

<210> SEQ ID NO 21
<211> LENGTH: 12
<212> TYPE: DNA
<213> ORGANISM: Glycine max

<400> SEQUENCE: 21
ttccaccaag tt                                                        12
```